(12) United States Patent
Wattiez et al.

(10) Patent No.: US 6,168,607 B1
(45) Date of Patent: Jan. 2, 2001

(54) DEVICE HAVING A FUNNEL FOR GUIDING SURGICAL TOOLS INTO A BODY CAVITY

(76) Inventors: Arnaud Wattiez, Rue Remeau, 63000 Clermont-Ferrand; Francis d'Arpiany, 40 Rue du Capitaine Selluez, 03110 Vendat, both of (FR)

(*) Notice: Under 35 U.S.C. 154(b), the term of this patent shall be extended for 0 days.

(21) Appl. No.: 09/265,705

(22) Filed: Mar. 8, 1999

Related U.S. Application Data

(63) Continuation of application No. 08/896,404, filed on Jul. 18, 1997, now Pat. No. 5,957,947.

(51) Int. Cl.[7] ..................................................... A61B 17/34
(52) U.S. Cl. .............................................................. 606/185
(58) Field of Search .................................. 606/164, 167, 606/283, 274, 174, 185; 604/264

(56) References Cited

U.S. PATENT DOCUMENTS 5,057,082 * 10/1991 Burchett, Jr. .......................... 604/164
5,478,329 * 12/1995 Ternamian ............................ 604/274
5,779,697   7/1998 Glowa et al. ......................... 606/185
5,868,773   2/1999 Danks et al. ......................... 606/185

* cited by examiner

Primary Examiner—Michael Buiz
Assistant Examiner—Vy Q Bui
(74) Attorney, Agent, or Firm—A. M. (Andy) Arismendi, Jr.

(57) ABSTRACT

The trocar assembly of the present invention includes a tubular body portion, a sleeve, a unidirectional sealing means included within the sleeve and a funnel portion mounted around the sleeve. A perforating tool is insertable through the funnel, through the unidirectional sealing means and thence through the tubular portion of the trocar assembly into the body of a patient. All portions of the trocar assembly of the present invention are formed from materials which may not be readily sterilized by immersion in a sterilizing bath or autoclaving. Thus, the single use trocar assembly of the present invention may be only used once and will be destroyed if an attempt is made to resterilize the entire trocar assembly or any portion thereof.

5 Claims, 2 Drawing Sheets

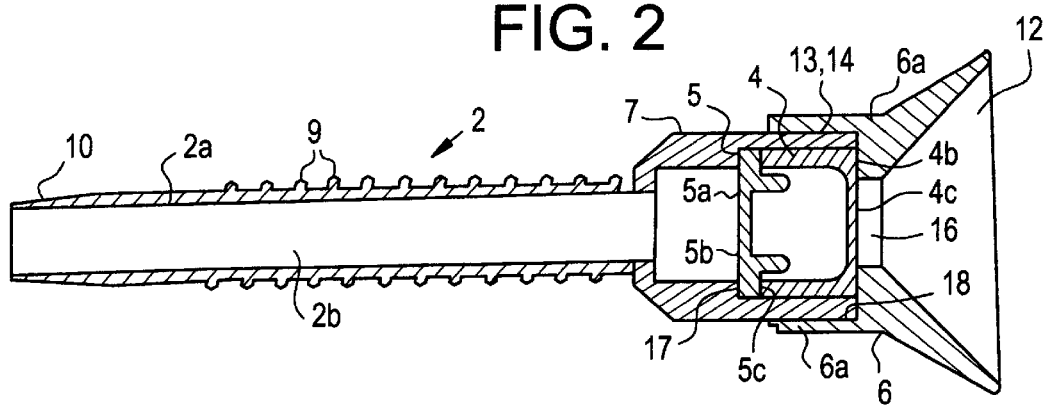
FIG. 2
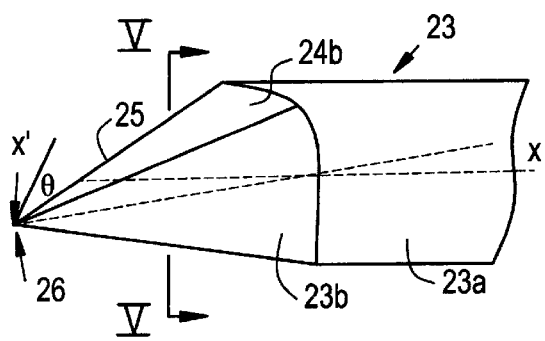
FIG. 3
FIG. 4    FIG. 5
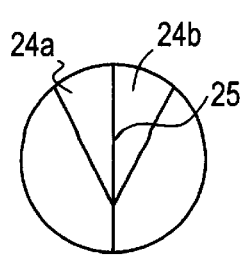
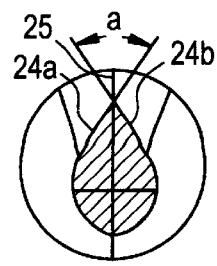
FIG. 6
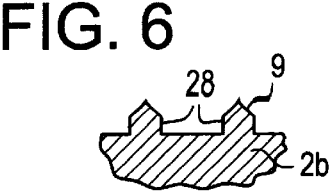

DEVICE HAVING A FUNNEL FOR GUIDING SURGICAL TOOLS INTO A BODY CAVITY

RELATED APPLICATION

This is a continuation of application Ser. No. 08/896,404, filed Jul. 18, 1997 of U.S. Pat. No. 5,957,947.

FIELD OF THE INVENTION

The present invention relates to a trocar assembly which includes a laparoscopic trocar and trocar sleeve (also called a cannula).

BACKGROUND

Laparoscopy is a method for the exploration of the peritoneal cavity wherein a sterile gas is blown or insufflated into the peritoneal cavity through the tubular portion or cannula section. The tubular portion or cannula section of the trocar assembly is connected to a gas source so that the pressure of the gaseous pocket within the peritoneal cavity may be maintained. This gaseous pocket within the peritoneal cavity is known as a pneumoperitoneum.

The visual exploration of the organs within the peritoneal cavity or other areas of the body is carried out by means of an endoscope or a similar device which passes through the tubular portion or cannula section of a trocar assembly after the tubular portion of a trocar assembly has been put in place in an abdominal wall. Similarly, one or more additional cannulas may be introduced into the pneumoperitoneum for the introduction of various tools to allow additional procedures such as biopsies.

The tubular portion or cannula section of the trocar assembly is a particularly important element, because it must pass through the flesh or tissue surrounding the peritoneal cavity without causing any postoperative trauma, yet still provide for anchorage to the abdominal wall. Above all, the tubular portion of the trocar assembly must assure that a seal is formed between the pneumoperitoneum and the atmosphere external to the peritoneal cavity.

Currently, most trocar assemblies are made of metal to facilitate their sterilization and re-use. Specifically, stainless steel is most commonly used. As far as the sealing means within the trocar assembly are concerned, other synthetic materials are used.

In general, the body portion of prior art trocar assemblies consists of a collection of detachable elements which allow access to the sealing means. After the insertion of the trocar assembly into the patient, the sealing means within the trocar assembly becomes contaminated by blood and other secretions. Thus, these prior art trocar assemblies must be disassembled and cleaned before they can be sterilized for reuse. Consequently, in prior art trocar assemblies that may be taken apart for cleaning, some type of connection means, threadable or otherwise, must be provided between the different parts of the trocar assembly. In some newer prior art trocar assemblies, synthetic materials are used in place of stainless steel. In these newer trocar assemblies, the synthetic materials which are used to seal the pneumoperitoneum from the atmosphere are generally not sterilizable. Such materials are described in European Patent Nos. A-564,373 and A-541,970.

The reusable character of the prior art trocar assemblies requires that they be made of expensive materials, or have a complex and expensive design. Complex and expensive designs provide significant drawbacks for the user. These drawbacks are in addition to those drawbacks which result from the cost of cleaning and re-sterilizing the trocar assemblies.

To overcome these drawbacks, it has been found that less expensive disposable trocar assemblies may be used. French Patent Nos. A-2,691,625 and A-2,694,181 disclose such disposable trocar assemblies. Despite the fact that the trocar assemblies are disposable, it has been found that some medical care personnel attempt to sterilize these disposable trocar assemblies for re-use.

French Patent No. A-2,691,625 defines the of a fibrous, synthetic material for making trocar assemblies. This fibrous, synthetic material is used for the manufacture of both the tubular body portion or cannula section of the trocar assembly, and, also the removable perforation device. Thus, the fibrous synthetic material allows for a reduction in the manufacturing cost of the trocar assembly, but it does not prevent reuse of the trocar assembly.

French Patent No. A-2,694,181 describes, more particularly, the structure of a sealing means in the tubular portion of cannula section of a trocar assembly. This patent does not address the problem of preventing reuse of the sealing means in a trocar assembly.

The object of the present invention is to provide a laparoscopic trocar assembly which is inexpensive to make, provides a seal to prevent the escape of gas back through the trocar assembly, and yet cannot be re-sterilized and used again Thus, once the trocar assembly is used it should be rendered unusable.

SUMMARY OF THE INVENTION

The trocar assembly of the present invention includes a tubular body portion or cannula section made of a synthetic material. The tubular body portion includes means which retain it in abdominal wall and also provides for the guidance of a removable device, typically a laparoscopic trocar, used to perforate the tissue surrounding the abdominal cavity. The removable device for perforation of the tissue surrounding the abdominal cavity is mounted so that it can slide axially within the tubular body portion. Also mounted within the tubular body portion are sealing means which are capable of cooperating with the perforation device, or with other types of surgical tools, to seal the perforated body cavity from the escape of gas. The sealing means includes a unidirectional closing means mounted within a sleeve at the end of the tubular body portion of the trocar assembly. The sleeve is further extendable by a guidance funnel, which is mounted on the external portion of the sleeve to be coaxial with the bore of the tubular body.

The unidirectional closing means is a shouldered disk which is mounted within the sleeve at the end of the tubular body portion of the trocar assembly. The shouldered disk unidirectional closing means is mounted under a socket within in the sleeve. The sleeve has a circular lip forming a sealing joint where it contacts the guidance funnel. The socket and the shouldered disk form a subassembly which is immobilized and permanently retained in the sleeve of the tubular body by a cover. The synthetic material from which this subassembly is formed is selected from those materials which cannot be sterilized by immersion in the type of sterilizing bath found in most hospitals. Similarly, the synthetic material from which the tubular body and the cover are made is selected from those materials which cannot be sterilized by insertion into the type of sterlizing autoclave found in most hospitals.

Because of the structure of the present invention, notably the locking of the cover to the sleeve portion to the tubular body, the subassembly which includes the unidirectional closing means and the sealing means cannot be extracted from the trocar assembly. This permanent mounting prevents, prior to any re-sterilization, the removal of any blood or secretions that may soil the subassembly. Moreover, the sterilization means conventionally used in hospitals, that is sterilization by autoclaving or sterilization by immersion in a sterilizing bath, will actually cause the partial destruction of one or more of the components of the trocar assembly. Specifically, sterilization by autoclaving or sterilization by immersion will destroy one or more of the tubular body portion, the cover, and the closing and sealing subassembly. The destruction of one or more parts of the trocar assembly renders it unusable.

As a result, the trocar assembly of the present invention, in addition to having a structure and a composition of a synthetic material, which leads to very low costs, cannot be resterilized by means readily available in a hospital environment. Consequently, any attempt to render a contaminated trocar assembly, made according to the present invention, reusable by either immersion bath sterilization or autoclave sterilization will render it unusable.

In one embodiment of the invention, the removable tissue perforation device is also made of a synthetic material. This removable tissue perforation device includes, at its end, a conical part having an angle at the center of between 35° and 50°, and two flat areas which form a dyhedron having an angle of between 60° and 75° The apical side of the dyhedron is slanted with respect to the longitudinal axis of the device by 20° to 40°. It also extends beyond longitudinal axis of the device to form an off-center tip.

This off-center tip combines the advantages of both a conical shape and a pyramidal shape without presenting any of their drawbacks. Such drawbacks are difficulty of penetration for the conical tip, and a traumatizing character for a pyramidal tip. In addition, the selected angles allow a cutting edge to be obtained using synthetic materials which do not have the same hardness as metals.

Other characteristics and advantages of the present invention will become apparent from the following description made with reference to the accompanying drawings in which one embodiment of the trocar assembly of the present invention is illustrated.

BRIEF DESCRIPTION OF THE FIGURES

FIG. 2 is a side view, in longitudinal section, of the trocar assembly, where its elements have been assembled one with another;

FIG. 3 is a partial side view, in elevation, of the tip of the perforation device;

FIG. 4 is an end view of the perforation device;

FIG. 5 is a cross-sectional view along V—V of FIG. 3;

FIG. 6 is a partial view in cross-section showing, in an enlarged scale, the shape of the threads provided on the tubular body.

DESCRIPTION OF THE EMBODIMENTS

Figure 1:
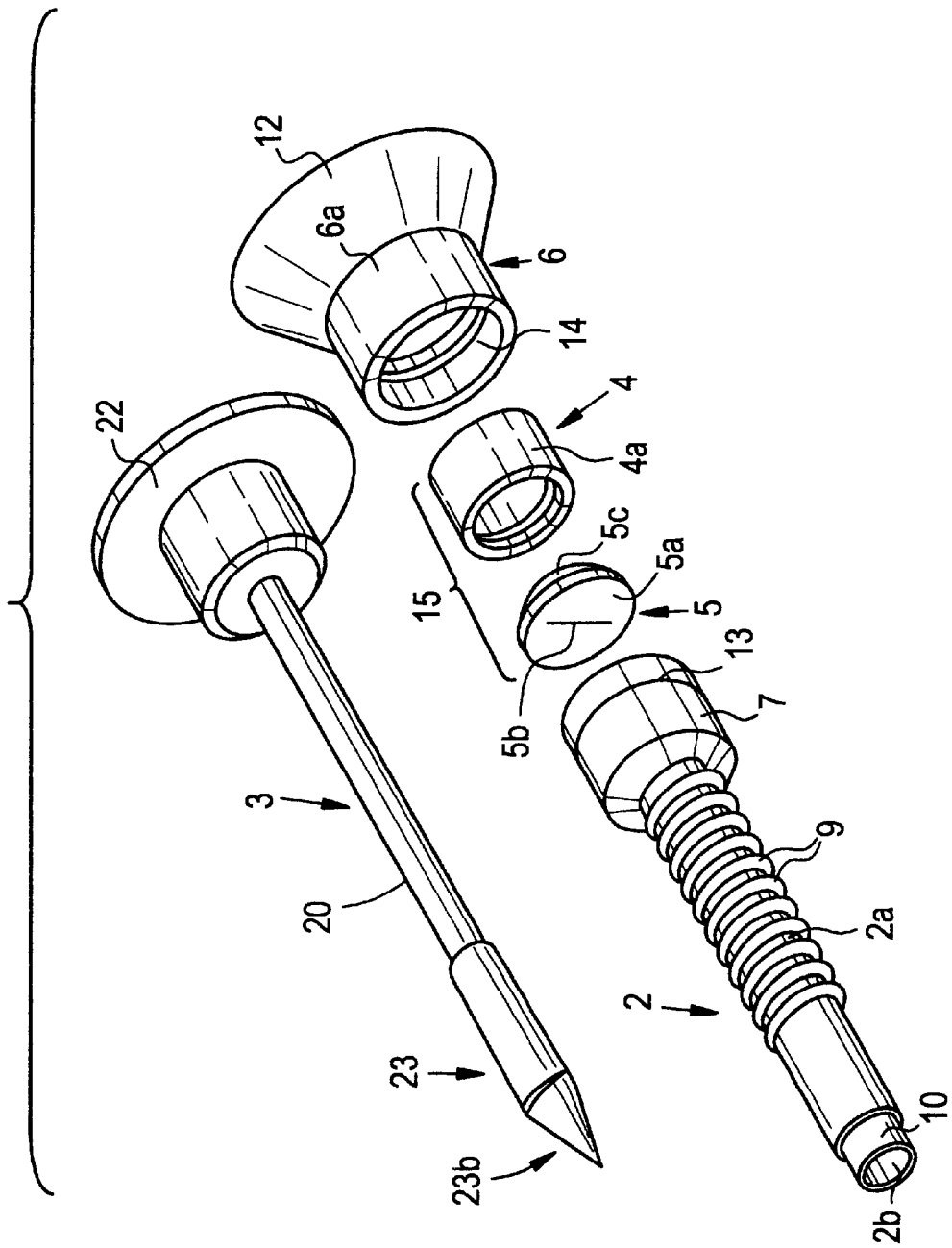
FIG. 1 is an exploded perspective view showing the different components of the trocar assembly of the present invention.

In general, the laparoscopic trocar assembly shown in the drawings consists of a tubular body portion 2, a removable perforation device 3, a sealing means 4, a unidirectional closing means 5, and a cover 6.

The tubular body portion 2 is integrally connected to a sleeve 7 which houses the sealing means 4 and the closing means 5. The tubular part 2a of the body 2 has external threadings 9 and it includes a beveled end 10 opposite the sleeve 7.

According to the invention, the tubular body portion 2 and the cover 6 are made of a synthetic material which cannot be sterilized in an autoclave, for example, polyethylene. The skirt 6a of the cover 6, which is slipped over the outside of the sleeve 7 of the body 2, is extended, outwardly by a funnel 12. The funnel 12 is coaxial with the bore 2b of the tubular body portion and it provides means for guiding one or more surgeon's tools through the tubular body portion 2. The permanent connection between the skirt 6a and the sleeve 7 is assured by a peripheral rib 13 which projects from sleeve 7, which in turn locks into a matching groove 14, provided inside the skirt 6.

FIG. 2 shows that, when these two elements are assembled, they firmly retain the subassembly 15 which includes the sealing means 4 and the unidirectional closing means 5 in the sleeve 7. The sealing means 4 and the unidirectional closing means S are advantageously made of a synthetic material such as a silicon elastomer which cannot be sterilized by immersion into a sterilizing bath, for example, a glutaraldehyde bath.

The unidirectional closing means 5 is a disk 5a which includes a diametral slit 5b and a shoulder 5c.

The sealing means is a socket 4a with a diametral wall 4b. A bore 16, shown in FIG. 2 delimits the sealing lip 4c. The shoulder Sc of the disk is slipped onto the end of the socket 4a to form the subassembly 15.

As shown in FIG. 2, the subassembly 15 is mounted directly within the interior of the sleeve 7, which is generally circular in shape. The subassembly 15 is immobilized as far as longitudinal translational movement by resting, on one side, against a shoulder 17 within the sleeve 7 and, on the other side, by the bottom 18 of the funnel assembly 12 which contacts sealing lip 4c on top of the sleeve 7.

The removable perforation device 3 is also made of a synthetic material. Specifically, the removable perforation device consists essentially of a rod 20 which has an integrally connected push button 22 on its external end and is integrally connected to a perforating head 23 on the opposite end. The perforating head 23 includes cylindrical part 23a, which ends in a conical part 23b.

FIGS. 3–5 show that the conical part 23b has an angle of 35° to 50° at its center. Preferably this angle is about 42°. The conical part 23b also includes two flat areas 24a, and 24b which transversely form a dyhedron whose angle a at the apex is from 60° to 75°. Preferably, this angle is about 68°. The apical edge 25 of the dyhedron is slanted with respect to the longitudinal axis, x'-x of the device 3 by an angle b having a value of about 20° to 40°. Preferably, this angle is about 24°, so that the tip 26 is off-center.

Because of the disclosed arrangement, the head 23 enables cutting, but it does not cause trauma, and the cutting is satisfactory even if the entire device 3 is made of a synthetic material which has a lesser hardness than steel, for example a polyacetal plastic.

It should be noted that the synthetic material which constitutes the removable device 3 for perforation is also selected from materials which cannot be sterilized at temperatures normally found in an autoclave.

After initial manufacture, the different elements of the trocar assembly are assembled and the perforation device 3 is put in place within the tubular body 2, and the entire trocar assembly is sterilized with ethylene oxide. Sterilization by ethylene oxide is expensive and not generally available to hospital departments which typically use sterilization by autoclaving at 140° C. or sterilization by immersion in a bath of a sterilizing liquid.

The use of the trocar assembly of the present invention is the same as that of existing prior art trocar assemblies. That is, after the area of tissue of the abdominal wall to be traversed has been identified, the surgeon presses the end of the tubular body 2 against this area. The surgeon then presses on the push rod of the perforation device 3, so that the head 23 of the perforation device perforates the body tissue. When the perforation is complete, the tubular body portion 2 is engaged in the tissue wall by guidance on the head 23, and then by threading the tubular body portion 2 in the tissue using the threads 9 formed on the exterior portion of the tubular body portion 2.

FIG. 6 shows that the threads 9 have a generally triangular shape, but with straight flanks 28 which improve the attachment to the threads 9 to bodily tissue.

This threading of the tubular body portion 2 into the tissue assures an excellent maintenance of the trocar assembly in the tissue wall. In combination with the funnel 12, the trocar assembly of the present invention facilities the guidance of the surgeon's tools. Additionally, it frees the hand of the surgeon who, when using prior art trocar assembly devices, had to hold the trocar during the introduction of a tool through the bore 2b of the insertion tube.

At the end of the examination or the operation, the trocar assembly is removed by simply unscrewing it and then discarding it, where it cannot be reused. Indeed, blood and other body secretions which contaminate the bore 2b, and also the subassembly 15, cannot be cleaned because the subassembly cannot be dismantled to be re-sterilization. Moreover, any attempt at re-sterilization by the means frequently used in hospital environments results in the partial destruction of one or more parts of the trocar assembly, that is destruction by melting of either the tubular body portion 2, the cover 6, or of the perforation device 3 by treatment in an autoclave and the destruction of the closing and sealing subassembly 15 in the case of sterilization by immersion in a sterilizing bath.

The risk of the reuse of an unclean and unsterilized trocar assembly is then made impossible for hospital personnel that have been informed about prophylactic procedures. In addition, the destruction of the trocar assembly of the present invention by attempts at re-sterilization makes the trocar effectively not reusable if re-sterilization is attempted.

While the single use trocar assembly of the present invention has been described by reference to its preferred emobodiment, those of ordinary skill in the art will understand that numerous other emobodiments may be made. Such other emobodiments shall fall within the scope and meaning of the appended claims.

We claim:

1. A single use non re-sterilizable device for guiding one or more surgical tools into a body cavity, said device comprising:
   (a) a tubular body portion, said tubular body portion having a first end and a second end, wherein
      said first end of said tubular body portion is constructed and arranged for insertion into a body cavity and
      said second end of said tubular body portion is formed into a sleeve, said sleeve having a first outside surface;
   (b) sealing means constructed and arranged to mount within said sleeve; and
   (c) a funnel having a guiding portion, a connecting portion and a central portion between the guiding portion and the connecting portion, wherein
      said connecting portion is attached to said sleeve opposite said tubular body portion with said sealing means located between said cental portion and said tubular body portion,
      said central portion has an opening which is substantially coaxial with the tubular body portion and allows access to the sealing means through the central portion when using the surgical tools,
      said guiding portion has a third end opposite said central portion, wherein said third end has an inside cross-sectional dimension perpendicular to the axis of the tubular body portion greater than the cross-sectional dimension of the first outside surface, and
      said guiding portion also has an interior surface conducive for guiding the surgical instruments to the opening in said central portion, when such surgical instruments are placed within the guiding portion for the purpose of insertion through said tubular body portion into the body cavity; said tubular body portion and/or said sealing means being fabricated from a synthetic material that will be destroyed and rendered unusable by immersion into a sterilizing bath or autoclaving.

2. The device of claim 1, wherein the interior surface of the guiding portion is has a truncated cone shape.

3. The device of claim 1, wherein the connecting portion is unreleaseably affixed to the sleeve.

4. In combination with a device for guiding one or more surgical tools into a body cavity, said device having at least (1) a tubular body portion, said tubular body portion having a first end and a second end, wherein said first end of said tubular body portion is constructed and arranged for insertion into a body cavity and said second end of said tubular body portion is formed into a sleeve, said sleeve having a first outside surface and (2) sealing means constructed and arranged to mount within said sleeve, a signal use non-resterilizable funnel, said funnel comprising:
   a guiding portion;
   a connecting portion; and
   a central portion between the guiding portion and the connecting portion, wherein
   said connecting portion is adapted for attachment to said sleeve opposite said tubular body portion such that said sealing means being located between said cental portion and said tubular body portion,
   said central portion has an opening which when the connecting portion is attached to the sleeve, the opening is substantially coaxial with the tubular body portion and allows access to the sealing means through the central portion when using the surgical tools,
   said guiding portion has a third end opposite said central portion, wherein said third end has an inside cross-sectional dimension perpendicular to the axis of the tubular body portion greater than the cross-sectional dimension of the first outside surface,
   said guiding portion also has an interior surface conducive for guiding the surgical instruments to the opening in said central portion, when such surgical instruments are placed within the guiding portion for the purpose of insertion through said tubular body portion into the body cavity;
   said funnel being fabricated from a synthetic material that will be destroyed and rendered unusable by immersion into a sterilizing bath or autoclaving.

5. The funnel of claim 4, wherein the interior surface of the guiding portion is has a truncated cone shape.

* * * * *